United States Patent
Lin et al.

(10) Patent No.: US 11,389,501 B1
(45) Date of Patent: Jul. 19, 2022

(54) METHOD FOR TREATING EYE INFLAMMATION USING ANTI-INFLAMMATORY COMPOSITION HAVING BIOACTIVE COMPOUND

(71) Applicant: TCI CO., LTD., Taipei (TW)

(72) Inventors: Yung-Hsiang Lin, Taipei (TW); Yu-Ling Wang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 17/329,169

(22) Filed: May 25, 2021

(30) Foreign Application Priority Data

Mar. 10, 2021 (TW) .................. 110108592

(51) Int. Cl.
*A61K 38/08* (2019.01)
*A61P 27/02* (2006.01)
*A23L 33/18* (2016.01)
*A61K 8/64* (2006.01)

(52) U.S. Cl.
CPC .............. *A61K 38/08* (2013.01); *A23L 33/18* (2016.08); *A61K 8/64* (2013.01); *A61P 27/02* (2018.01)

(58) Field of Classification Search
CPC ............................... A61K 38/08; A61P 27/02
See application file for complete search history.

*Primary Examiner* — Lianko G Garyu
(74) *Attorney, Agent, or Firm* — Chieh-Mei Wang

(57) ABSTRACT

A method for treating eye inflammation by using an anti-inflammatory composition is provided. The bioactive compound in the anti-inflammatory composition is a peptide having an amino acid sequence as set forth in SEQ ID NO.: 1. The amino acid sequence is a peptide fragment derived from cowhide. The composition may be administered to the eye of a human subject for reducing the expression of vascular endothelial growth factor A (VEGFA) gene, interleukin-1 beta (IL-1β) gene, and/or interleukin-8 (IL-8) gene.

8 Claims, 3 Drawing Sheets

Specification includes a Sequence Listing.

SEQUENCE LISTING

<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: synthesized

<400> SEQUENCE: 1

Thr Lys Leu Pro Ser Gly Leu Pro Val Ser Leu
1               5                   10

<210> SEQ ID NO 2
<211> LENGTH: 20
<212> TYPE: DNA
<213> ORGANISM: Artificial Sequence
<220> FEATURE:
<223> OTHER INFORMATION: synthesized

<400> SEQUENCE: 2
ccttgctgct ctacctccac                                              20

<210> SEQ ID NO 3
<211> LENGTH: 20
<212> TYPE: DNA
<213> ORGANISM: Artificial Sequence
<220> FEATURE:
<223> OTHER INFORMATION: synthesized

<400> SEQUENCE: 3

-continued

```
atctgcatgg tgatgttgga                                              20

<210> SEQ ID NO 4
<211> LENGTH: 20
<212> TYPE: DNA
<213> ORGANISM: Artificial Sequence
<220> FEATURE:
<223> OTHER INFORMATION: synthesized

<400> SEQUENCE: 4
agctacgaat ctccgaccac                                              20

<210> SEQ ID NO 5
<211> LENGTH: 22
<212> TYPE: DNA
<213> ORGANISM: Artificial Sequence
<220> FEATURE:
<223> OTHER INFORMATION: synthesized

<400> SEQUENCE: 5
cgttatccca tgtgtcgaag aa                                           22

<210> SEQ ID NO 6
<211> LENGTH: 22
<212> TYPE: DNA
<213> ORGANISM: Artificial Sequence
<220> FEATURE:
<223> OTHER INFORMATION: synthesized

<400> SEQUENCE: 6
ttttgccaag gagtgctaaa ga                                           22

<210> SEQ ID NO 7
<211> LENGTH: 21
<212> TYPE: DNA
<213> ORGANISM: Artificial Sequence
<220> FEATURE:
<223> OTHER INFORMATION: synthesized

<400> SEQUENCE: 7
aaccctctgc acccagtttt c                                            21

<210> SEQ ID NO 8
<211> LENGTH: 19
<212> TYPE: DNA
<213> ORGANISM: Artificial Sequence
<220> FEATURE:
<223> OTHER INFORMATION: synthesized

<400> SEQUENCE: 8
ctgggctaca ctgagcacc                                               19

<210> SEQ ID NO 9
<211> LENGTH: 21
<212> TYPE: DNA
<213> ORGANISM: Artificial Sequence
<220> FEATURE:
<223> OTHER INFORMATION: synthesized

<400> SEQUENCE: 9
aagtggtcgt tgagggcaat g                                            21
```

METHOD FOR TREATING EYE INFLAMMATION USING ANTI-INFLAMMATORY COMPOSITION HAVING BIOACTIVE COMPOUND

CROSS-REFERENCE TO RELATED APPLICATION

This non-provisional application claims priority under 35 U.S.C. § 119 (a) to Patent Application No. 110108592filed in Taiwan, R.O.C. on Mar. 10, 2021, the entire contents of which are hereby incorporated by reference.

REFERENCE OF AN ELECTRONIC SEQENCE LISTING

The contents of the electronic sequence listing (P211767USI_ST25.txt; Size:2.027 KB; and Date of Creation: Mar. 10, 2021) is herein incorporated by reference in its entirety.

BACKGROUND

Technical Field

The present disclosure relates to use of a bioactive compound, and in particular relates to a method for treating inflammation using an anti-inflammatory composition having a bioactive peptide.

Related Art

With rapid development of technological products, modern people spend a lot of time using mobile phones and computers, causing a gradual increase in the burden on the eye, and problems such as deterioration of visual function and xerophthalmia. Therefore, eye protection is a topic that the society attaches great importance to today. In addition, the damage caused by blue light to the eye cannot be ignored, and may even cause eye inflammation and other symptoms.

Clinical symptoms of eye inflammation include bloodshot eyes, itchy eyes, conjunctival edema, eyelid swelling, tearing, and the like, which are caused by activation of vascular endothelial cell receptors due to external stimulation, leading to vasodilation and increased vascular permeability. In turn, inflammatory factors such as 1L-1β and 1L-8 enter the blood vessels, white blood cells enter the conjunctival tissues, and ultimately inflammation is caused. Common diseases associated with eve inflammation include allergic conjunctivitis and the like.

Collagen is an important protein in the human body, is widely present in the connective tissues, and can lubricate joints and keep skin elastic. With the loss of collagen, the skin would have wrinkles and become sagging. In addition to being the main component of human ligaments, extracellular matrix and other tissues, collagen is also the main component of the cornea of the eye.

Nowadays, the society urgently needs a healthcare and nutritional product that can effectively protect the eye. However, there has not been much research on exploring the protective effects of collagen-related peptides on the eye. In addition, whether fragments of specific collagen-related peptides have eye protective or anti-inflammatory effects remains to be clarified,

SUMMARY

In view of the foregoing, an objective of the present disclosure is to provide a bioactive compound for use in preparation of an eye protective and/or anti-inflammatory composition. The bioactive compound is a peptide, and the peptide has an amino acid sequence as set forth in SEQ ID NO.: 1. The amino acid sequence is a peptide fragment derived from cowhide.

Another objective of the present disclosure is to provide a method for treating inflammation in a human in need thereof. The method includes administering to the human a therapeutically effective amount of an anti-inflammatory composition. The composition includes a bioactive compound. The bioactive compound is a peptide having an amino acid sequence as set forth in SEQ ID NO.: 1.

In some embodiments, the amino acid sequence can be isolated and purified from cowhide cells, cowhide collagen, or beef cells.

In some embodiments, the amino acid sequence can be synthesized by Fmoc-solid phase peptide synthesis or other chemical synthesis methods.

In some embodiments, the composition is used to reduce the expression of inflammation-related genes, and the inflammation-related genes include at least one of vascular endothelial growth factor A (VEGFA) gene, interleukin-1 beta (IL-1β) gene, and interleukin-8(IL-8) gene.

In some embodiments, the concentration of the bioactive compound in the composition is at least 0.0125 mg/mL, In some embodiments, the composition is administered to an eye of the human.

In some embodiments, the eye protective effect of the composition includes preventing eye inflammation, resisting blue light, relieving eye fatigue, and reducing light damage to the eye.

In some embodiments, the composition is a medicament, a food or a skincare product.

In some embodiments, the food is a health food.

In summary, the present disclosure provides a method for treating inflammation using a bioactive compound. The bioactive compound is a peptide, and the peptide has an amino acid sequence as set forth in SEQ ID NO : 1. The amino acid sequence is a peptide fragment derived from cowhide. The amino acid sequence can reduce the expression of inflammation-related genes, which may include at least one of vascular endothelial growth factor A (VEGFA) gene, interleukin-1 beta (IL-1β) gene, and interleukin-8 (1L-8) gene, thereby achieving the effects of preventing eye inflammation, resisting blue light, relieving eye fatigue, reducing light damage to the eye, delaying the decline in visual function, preventing xerophthalmia, resisting inflammation, and the like.

DETAILED DESCRIPTION

Figure 1:
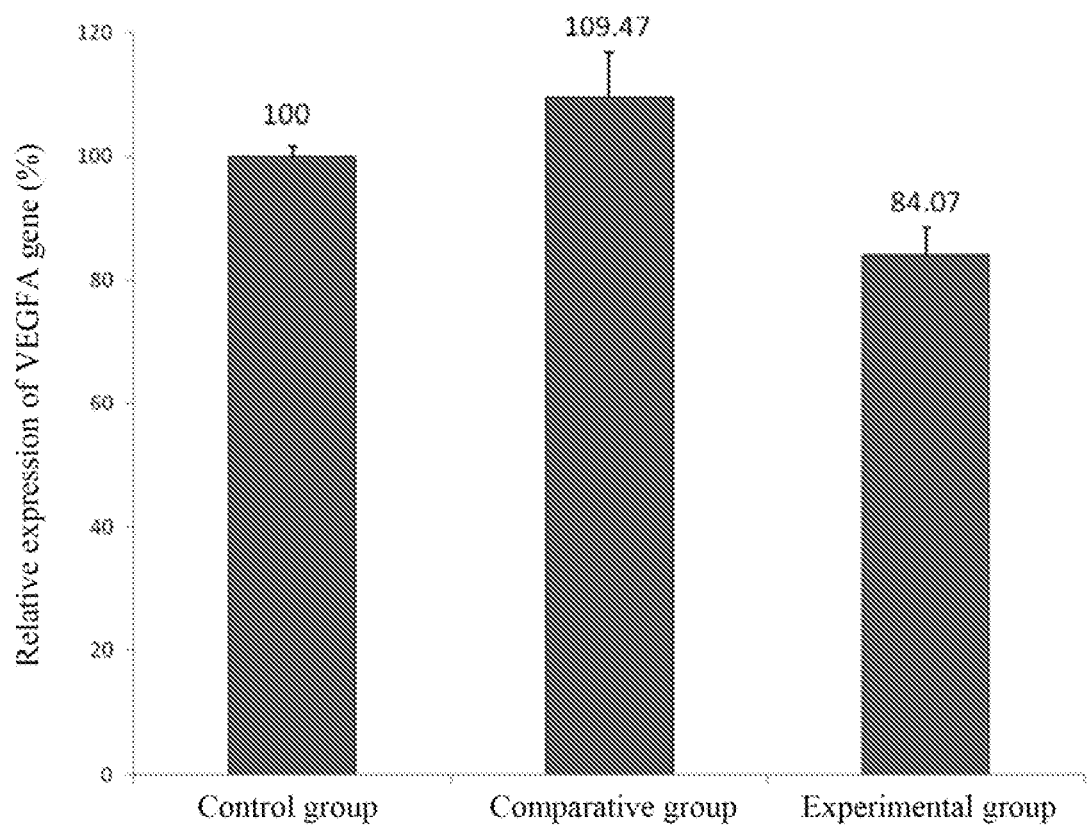
FIG. 1 is a bar chart showing a relative ratio of VEGFA gene expression in each group in Embodiment 3 of the present disclosure.

The following will further describe some of the specific implementation of the present invention in conjunction with the drawings. The following embodiments are used to illustrate the present invention and are not intended to limit the scope of the present invention. Anyone familiar with the art can make some changes and modifications without departing from the spirit and scope of the present invention, and the scope of protection should not he limited to the conditions specified in the description.

In the present disclosure, Excel software is used for statistical analysis. Data are expressed as mean ±standard deviation (SD), and the difference between groups is analyzed by student's t-test. In the diagram, "*" represents $p<0.05$, "" represents $p<0.01$, and "*" represents $p<0.001$. The more the "*", the more significant the statistical difference.

In some embodiments,, any of the aforementioned compositions may he an edible composition. In other words, the edible composition contains a specific amount of the bioactive compound. In some embodiments, the aforementioned edible compositions may be a food product or a food additive. In some embodiments, the food product may be, but is not limited to, beverages, fermented foods, bakery products, health foods, or dietary supplements.

In some embodiments, the peptide can be used as the bioactive compound for preparing an eye protective and/or anti-inflammatory composition. The bioactive compound is a peptide, and the peptide has the amino acid sequence as set forth in SEQ ID NO: 1. The amino acid sequence is a peptide fragment derived from cowhide.

It should be understood that "peptide" is a substance between amino acids and proteins, and consists of a plurality of amino acids. In addition, the peptide as the bioactive compound may be an "isolated peptide" or a "synthesized peptide." The "isolated peptide" may refer to a peptide fragment isolated from an organism or a derivative of an organism, and the peptide fragment has bioactivity. The "synthetic peptide" may refer to a peptide fragment synthesized according to a desired amino acid sequence by means of instruments or experimental operations, and the peptide fragment has bioactivity.

In some embodiments, the peptide as the bioactive compound can be isolated from a peptide fragment derived from cowhide or synthesized by instruments or experiments. For example, the sources of peptide fragments derived from cowhide may include cowhide cells, cowhide collagen, and beef cells. The main ingredient in cowhide is collagen, but in the process of extracting cowhide collagen from cowhide, in addition to the mainly extracted cowhide collagen, proteins in cowhide cells (i.e., cowhide cell proteins) and proteins in the beef cells that remains on the cowhide (i,e., beef cell proteins) would also be extracted. It should be understood that the term "peptide fragments derived from cowhide" mentioned herein refers to peptide fragments that are mainly composed of collagen and contains cowhide cell proteins and beef cell proteins as well.

In some embodiments, the peptide fragments derived from cowhide may include peptide fragments of at least one of collagen, procollagen, cowhide cell protein, beef cell protein, or a combination thereof. For example, the collagen may be type IV collagen, type V procollagen, type XIV collagen, and the like.

For example, collagen peptide raw materials derived from cowhide can be isolated to obtain the amino acid sequence as set forth in SEQ ID NO.: 1, and the collagen peptide raw materials include peptide fragments of cowhide collagen, peptide fragments of cowhide cell protein, and/or peptide fragments of beef cell protein. In one embodiment, the collagen peptide raw material may be German bovine collagen peptide powder (purchased from GELITA, Germany), or collagen peptide powder obtained by enzymatic hydrolysis of collagen extracted from cowhide followed by drying.

In some embodiments, the peptide as the bioactive compound can be isolated from cowhide collagen peptide powder by instruments (e.g., fast protein liquid chromatography system and high performance liquid chromatography system). In addition, the aforementioned isolation step obtains the amino acid sequence as set forth in SEQ ID NO.: 1 by utilizing peptide properties (such as molecular weight, hydrophilicity, hydrophobicity, polarity, non-polarity, or other physical or chemical properties).

In some embodiments, the amino acid sequence can be synthesized by Fmoc-solid phase peptide synthesis or other chemical synthesis methods.

In some embodiments, the composition prepared from peptides containing the amino acid sequence as set forth in SEQ ID NO.: 1 is used to reduce the expression of inflammation-related genes, which may include at least one of vascular endothelial growth factor A (VEGFA) gene, Interleukin-1 beta (IL-1β) gene, and Interleukin-8 (IL-8) gene.

In some embodiments, the concentration of the bioactive compound in the composition is at least 0.0125 mg/mL.

In some embodiments, the bioactive compound according to an embodiment of the present disclosure is used to prepare an eye protective and/or anti-inflammatory composition, the eye protective effect of which may include preventing eye inflammation, resisting blue light, relieving eye fatigue, and reducing light damage to the eye.

In some embodiments, the composition may be a medicament, a food, or a skincare product. The food may be a health food.

In some embodiments, any of the aforementioned compositions may be an edible composition. In some embodiments, the edible composition may be made into a food product or may be a food additive. That is, the food product is prepared by adding the edible composition during the preparation of a food ingredient by a conventional method, or the edible composition is added during the production process of the food product. Herein, the food product may be a product formulated with edible ingredients for human or animal consumption.

In some embodiments, the food product may be, but is not limited to, beverages, fermented foods, bakery products, health foods, and dietary supplements.

Embodiment 1: Isolation of peptide from cowhide collagen

First, 100 mg of cowhide collagen peptide powder (purchased from GELITA, Germany) was weighed, and dissolved in 5 ml of buffer A to obtain a collagen peptide solution. The buffer A was prepared with 50 millimolar (mM) Tris/HCl buffer (pH 8.0) and 100 mM of sodium chloride (NaCl).

Then, the collagen peptide solution was crudely isolated using a fast protein liquid chromatograph instrument (FPLC purification instrument, AKTA GE Healthcare Life Sciences, hereinafter referred to as a purification instrument) to obtain an crude peptide mixture. A separation column loaded in the purification instrument was a molecular sieve colloidal purification column (sephadex G-25, 2.6 cm×10 cm, 53 ml). The flow rate of the purification instrument was set at one milliliter per minute (1 mL/min). The wavelength of ultraviolet light used for peptide detection was 220 nanometers (nm). Portions of the crude peptide mixture having a peak measurement value corresponding to 5 kDa or less were freeze-dried (instrument: EYELA; model: FD-1000) at −80° C. for 12 hours to obtain a solid crude peptide mixture.

30 mg of the solid crude peptide mixture was weighed and dissolved in 2 ml of secondary deionized water containing 0.1% trifluoroacetic acid (TFA) to obtain a pre-isolated peptide mixture. Next, the pre-isolated peptide mixture was isolated through a high-performance liquid chromatography (HPLC) system (Hitachi Chromaster HPLC system, Hitachi, Tokyo, Japan; hereinafter referred to as HPLC system) to obtain multiple groups of isolated peptides. A molecular sieve C18 high-pressure column (TSKgel G2000SWXL, Tosoh, 30 cm×7.8 mm, 5 μm) was loaded in the HPLC system. A buffer solution A (0.1% TEA dissolved in 100% deionized water) and a buffer solution B (0.1% TFA dissolved in 100% ACN) were mixed according to the separation gradient set in the HPLC system. The separation gradient was 5% acetonitrile (ACN)/0.1% TFA to 100% ACN/0.1% TFA (that is, the concentration of ACN was increased from 5% to 100% in 0.1% of TFA), the flow rate was set at one milliliter per minute (1 mL/min) and the column temperature was set at 40'C.

Herein, the peptides in the crude peptide mixture were eluted by HPLC based on different polarities and molecular weights of the peptides, resulting in multiple groups of isolated peptides. In addition, the multiple groups of isolated peptides were freeze-dried (instrument: EYELA; model: FD-1000) at −80° C. for 12 hours to obtain multiple groups of solid isolated peptides.

(mass-to-charge ratio) to 1200 m/z, Under the CID data-dependent acquisition mode, the detection range for the peptides was set at 100-5000daltons (Da).

Peptides are easily broken at the peptide bonds in the gaseous environment of the mass spectrometer. The a, b, and c ion series are N-terminal fragments broken at different positions; x, y, and z ion series are C-terminal fragments; and numerals are used to represent the order of an amino acid sequence. The entire peptide sequence can be calculated from the mass differences among the same series of fragments (such as y1, y2, y3 . . . ), thereby identifying the amino acid sequence of SEQ ID NO.: 1, and molecular weights thereof.

TABLE 1

| Sequence number | Sequence | Molecular weight (Da) |
| --- | --- | --- |
| SEQ ID NO.: 1 | TKLPSGLPVSL | 1110.66 |

As shown in Table 1, in some embodiments, the molecular weight of the amino acid sequence Of the isolated peptidel was 1110.66, and the chemical structure thereof is shown as follows:

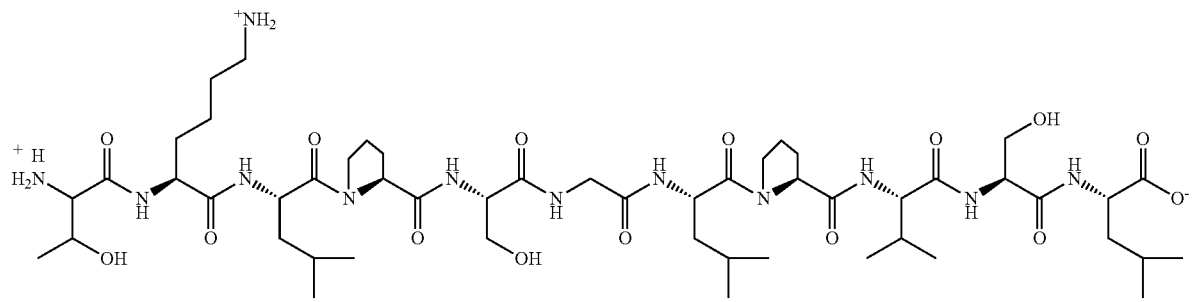

Embodiment 2: Identification of peptides derived from cowhide collagen

The multiple groups of isolated peptides in Embodiment 1 were subjected to protein identification. First, the multiple groups of solid isolated peptides were dissolved in deionized water to a concentration of 20 mg/ml; then, protein identification was performed by a liquid chromatography mass spectrometer (LC-MS/MS). In addition, the LC-MS/MS was a quadrupole-time-of-flight tandem mass spectrometer system (Q-TOF). The model of the liquid chromatography system (LC system) was UltiMate 3000 RSLCnano LC Systems (Thermo Fisher Scientific), and the model of the mass spectrometer was TripleTOF®6600 System (Applied Biosystems Sciex).

The separation column loaded in the liquid chromatography system was a C18separation column (Acclaim Pep-Map C18, 75 μm I.D.×25 cm nanoViper, 2 μm, 100 Å (Thermo Fisher Scientific)). The solution system used in the LC-MS was a buffer solution A (0.1% TFA dissolved in 100% deionized water) and a buffer solution B (0.1% TFA dissolved in 100% ACN). The separation gradient set in the LC-MS was from 5% buffer solution B to 90% buffer solution B, the flow rate was set at 300 nanoliters per minute (300 nl/min), and the gradient lasted for 30 minutes.

In the settings of the mass spectrometer, survey scan was set to scan all ionized isolated peptides in a range of 400 m/z Therefore, the cowhide collagen peptide raw material was shown to contain the isolated peptide having the amino acid sequence of SEQ 10 NO.: 1.

Embodiment 3: Synthesis of peptides derived from cowhide collagen

In order to verify the eye protective effect of the isolated peptide identified in Embodiment 2, in Embodiment 3, a synthesized peptide was prepared according to the amino acid sequence identified in the foregoing Embodiment (i.e., SEQ ID NO.: 1). The synthesis method used was Fmoc-solid phase peptide synthesis, and the instrument used was a peptide synthesizer (Focus XC III 0, AAPPTEC, USA).

The amino acid sequence of SEQ ID NO.: 1 was identified as Thr-Lys-Leu-Pro-Ile-Gly-Pro-Ser-Gly-Leu-Pro-Val-Ser-Leu.

Step 1: First, resin was placed in a reaction vessel. 15 ml of dichloromethane (DCM) was added to the reaction vessel per 1 gram of resin. The resin was soaked in dichloromethane for 30 minutes to make the resin swell in the solution.

Step 2: DCM in the reaction vessel was removed. 15 ml of 20% piperidine dimethyl formamide (piperidine DMF) was added per 1 gram of resin to the reaction vessel to react with the resin for 5 minutes. Then, the solution in the reaction vessel was removed. 15 ml of 20% piperidine DMF was added per 1 gram of resin to the reaction vessel again to react with the resin for 15 minutes to remove the protective groups from the resin, thus obtaining deprotected resin.

Step 3: After the solution in the reaction vessel was removed again, a few resin particles were taken from the reaction vessel for detection. First, the resin was rinsed three times with ethanol, and added one drop of ninhydrin and one drop of phenol solution. The mixture was heated at 105-110° C. for 5 minutes. If the ninhydrin and phenol solution reacted with the resin and turned dark blue, a positive reaction was suggested, indicating that the resin in the reaction vessel had been deprotected and could bind with amino acids.

Step 4: 10 ml of DMF was added per 1 gram of the deprotected resin to the reaction vessel, and the resin was repeatedly rinsed for 6 times.

Step 5: A three-fold excess of Fmoc-protected threonine (Fmoc-Thr) and a three-fold excess of hydroxybenzotriazole (HOBt) were dissolved with a small amount of DMF. The solution was added to the reaction vessel to react with the deprotected resin for 90 minutes.

Step 6: After 90 minutes of reaction, 10 ml of DMF was added per 1 gram of resin to the reaction vessel to rinse the resin attached with a threonine (Thr) for 3 times.

Then, the aforementioned steps (2) to (6) were repeated until the remaining ammo acids (Lys, Leu, Pro, Ile, Gly, Pro, Ser, Gly, Leu, Pro, Val, Ser, and Leu) were sequentially attached to the resin to form a primary synthetic peptide with the amino acid sequence of SEQ ID NO.: 1.

Step 7: 10 ml of DMF was added per 1 gram of resin to the reaction vessel to rinse the primary synthetic peptide for 3 times. Then 10 ml of DCM was added per 1 gram of resin to the reaction vessel to rinse the primary synthetic peptide for 3 times. Finally, 10 ml of ethanol was added per 1 gram of resin to the reaction vessel to rinse the primary synthetic peptide for 3 times.

Step 8: The rinsed primary synthetic peptide was reacted with 10 grams of lysate (86% trifluoroacetic acid, 4% thioanisole, 3% water, 5% ethanedithiol (EDT) and 2% phenol) for 120 minutes to isolate the primary synthetic peptide from the resin.

Step 9: The lysate containing the primary synthetic peptide was isolated from the resin through a sand core funnel, and then the lysate containing the primary synthetic peptide was added to ether that was eight times the volume of the lysate. Then, the primary synthetic peptide and the lysate were isolated by suction filtration using a Buchner funnel. After the ether containing the lysate was suction dried, the primary synthetic peptide was rinsed with ether for 3 times. At this moment, the primary synthetic peptide was solid. After the ether was volatilized at room temperature, a dried primary synthetic peptide was obtained.

Step 10: 1 mg of the dried primary synthetic peptide was redissolved in 0.5 ml of deionized water. 20 ml of the redissolved primary synthetic peptide was isolated and purified by an HPLC system (Model Hitachi Chromaster HPLC system, Hitachi, Tokyo, Japan) to obtain a pure synthetic peptide. A C18 column (Gemini-NX) was loaded in the HPC system and the detection wavelength was set at 220 nm. In the HPLC system, a buffer solution A (0.1% TFA dissolved in 100% deionized water) and a buffer solution B (0.1% TFA dissolved in 100% ACN) were mixed according to a linear separation gradient to elute and isolate the synthetic peptide. The separation gradient was a linear gradient from 10% buffer solution B to 90% ACN (dissolved in 0.1% TFA), the flow rate was set at 1 mL/min and the separation time was set at 30 minutes. By calculating the peak area of each synthetic peptide in the HPLC chromatogram, the purity of the synthetic peptides was over 95%. Consequently, a synthetic peptide having an amino acid sequence as set forth in SEQ ID NO.: 1 was obtained.

Embodiment 4 : Efficacy test of the composition on eye protection and anti-inflammatory genes regulation In the present embodiment, an RNA extraction kit, a reverse transcriptase, and a KAPA SYBR® FAST qPCR reagent kit were used in conjunction with a quantitative PCR instrument to determine the changes in expression level of the genes associated with eye protection and anti-inflammation in human retinal pigment epithelial cells treated with the peptide having the amino acid sequence of SEQ ID NO.: 1. Further, the efficacy of the bioactive compound obtained from the cowhide peptides of the present disclosure in resisting blue light and preventing inflammatory reactions was confirmed.

For example, the inflammation-related genes may include vascular endothelial growth factor A (VEGFA) gene, interleukin-1 beta (IL-1β) gene, and interleukin-8 (IL-8) gene, which are genes that up-regulate and elicit inflammatory reactions when the eye is stimulated by the external environment. Therefore, regulation of the inflammation-related genes is associated with eye protection.

The protein encoded by the VEGFA gene plays an indispensable role in angiogenesis, and is associated with permeability of blood-retinal and blood-brain barriers. VEGFA protein induces the tyrosin kinase pathway to activate the endothelial nitric oxide synthase (eNOS) and other enzymes, thereby increasing vascular permeability and angiogenesis. In addition to angiogenesis, the VEGFA protein is also involved in the maintenance of the vascular system. Specific binding of the VEGFA protein is associated with maturation of blood vessels in various tissues (e.g., heart, kidney and brain), and VEGFA possesses important functions in maintaining static vascular endothelium and promoting inflammation.

Proteins encoded by the interleukin-1 beta (IL-1β) and interleukin-8 (IL-8) genes are important regulators of inflammatory reactions, and belong to the interleukin family. The interleukin family includes 11 proteins, which form a complex network that promotes inflammation. Proteins of the interleukin family are expressed as white blood cells and endothelial cells are stimulated by the external environment, thereby activating and controlling inflammatory reactions. Therefore, IL-1β and IL-8 are considered pro-inflammatory proteins.

Therefore, in Embodiment 4, VEGFA gene, IL-1β gene and IL-8 gene were used as the analytic targets for verifying the efficacy of the bioactive compound of the present disclosure on eye protection and anti-inflammation.

Materials and instruments

1. Cell strain: Human retinal pigment epithelial cell ARPE-19 (purchased from ATCC, product number CRL-2302).

2. Medium: DMEM medium (Gibco, product number 11965-092) and Hans F12 medium (Gibco, product number 31765035) were mixed in a volume ratio of 1:1, and 10% fetal bovine serum (Gibco, product number 10437-028), 0.5 mM of sodium pyruvate (Gibco, product number 11360-070) and 15 mM of HEPES buffer (Gibco, product number 15630106) were then added.

3. RNA extraction reagent kit (purchased from Geneaid, product number Lot No. FC24015-G).

4. Reverse transcriptase (Super Script® 111 Reverse Transcriptase), purchased from Invitrogen, USA, product number 18080-051.

5. Primers for measurement target genes, including VEGFA gene, IL-1β gene, IL-8 gene, and GAPDH gene (as internal control).

6. KAPA SYBR® FAST qPCR reagent kit (purchased from Sigma, product number 38220000000).

7. ABI StepOnePlus™ Real-Time PCR system, purchased from Thermo Fisher Scientific.

8. Experiment samples: The experiment samples used in the present embodiment is a bioactive compound, particularly a cowhide peptide, which is the synthetic peptide of SEQ ID NO.: 1 obtained in Embodiment 3 (hereinafter referred to as cowhide peptide).

Experiment procedure

Cell culture stage:

First, $1.5 \times 10^5$ human retinal pigment epithelial cells were placed into a six-well cell culture plate containing 2 ml of the aforementioned medium per well, and incubated at 37° C. for 24 hours.

Cell treatment stage:

Then, the human retinal pigment epithelial cells in each well were divided into three groups: a control group, a comparative group (treated with blue light), and an experimental group (added with the cowhide peptide of the present disclosure and treated with blue light), according to the following test conditions. Experiments were repeated for 3 times, and the experimental conditions are as shown in Table 2:

TABLE 2

Experiment design

| Group | Concentration of experiment sample | Experimental control |
|---|---|---|
| Control group | N/A | Incubated for 24 hours |
| Comparative group | N/A | After incubated for 24 h, and irradiated with blue light for 15 min. |
| Experimental group | Cowhide peptide, 0.0125 mg/ml | After incubated for 24 h, and irradiated with blue light for 15 min. |

In detail, during the cell treatment stage, the human retinal pigment epithelial cells in the control group and the comparative group were incubated in 2 ml of culture medium, whereas in the experimental group, the cowhide peptide prepared according to Embodiment 3 was added to the medium to reach a concentration of 0.0125 mg/ml. Each group was incubated at 37° C. for 24 hours.

After incubated for 24 hours, the comparative group and the experimental group were irradiated with blue light for 15 minutes.

Cell analysis stage:

The cell membranes of each group of human retinal pigment epithelial cells (i.e., the control group, the comparative group, and the experimental group) resulted from the cell treatment stage were broken with cell lysates. Then, RNA in the cell solution of each group was extracted by the RNA extraction reagent kit (Geneaid, Taiwan, Lot No. FC24015-G). Then, 1000 nanograms (ng) of the extracted RNA of each group was used as a template, and reversely transcribed into corresponding cDNA by SuperScript® III reverse transcriptase (Invitrogene, USA, product number 18080-051). Then the cDNA of each group was subjected to a quantitative real-time reverse transcription polymerase chain reaction (qRT-PCR) using the ABI StepOnePlus™ Real-time PCR system (Thermo Fisher Scientific), KAPA SYBR FAST (Sigma, USA, product number 38220000000) and the primers listed in Table 3 (SEQ 1D NO.: 2 to SEQ ID NO.: 9) to assess the expression of VEGFA gene. IL-8gene, and IL-1β gene in the human retinal pigment epithelial cells of each group. The instrument setting for the qRT-PCR was 95° C. for 20 seconds, 95° C. for 3 seconds, 60° C. for 30 seconds, and repeated for 40 cycles. Gene quantification was performed using a $2^{-\Delta Ct}$ method. Here, mRNA expression of the VEGFA gene, IL-8 gene and IL-1β gene can be quantified using the gRT-PCT of the cDNA. Then the expression, of the protein encoded by the VEGFA gene, IL-8 gene and IL- 1β gene was determined.

TABLE 3

| Gene | Primer name | Sequence number | Primer sequence |
|---|---|---|---|
| VEGFA | VEGFA-F | SEQ ID NO.: 2 | CCTTGCTGCTCTACCTCCAC |
| | VEGFA-R | SEQ ID NO.: 3 | ATCTGCATGGTGATGTTGGA |
| IL-1β | IL-1β-F | SEQ ID NO.: 4 | AGCTACGAATCTCCGACCAC |
| | IL-1β-R | SEQ ID NO.: 5 | CGTTATCCCATGTGTCGAAGAA |
| IL-8 | IL-8-F | SEQ ID NO.: 6 | TTTTGCCAAGGAGTGCTAAAGA |
| | IL-8-R | SEQ ID NO.: 7 | AACCCTCTGCACCCAGTTTTC |
| GAPDH | GAPDH-F | SEQ ID NO.: 8 | CTGGGCTACACTGAGCACC |
| | GAPDH-R | SEQ ID NO.: 9 | AAGTGGTCGTTGAGGGCAATG |

Refer to FIG. 1, when the expression of VEGFA gene in the control Luoup is regarded as 100%, the expression of gene in the comparative group relative to the control group was 109.47%, confirming that after irradiation with blue light, the expression of VEGFA gene in the human retinal pigment epithelial cells upregulated, and inflammation was promoted. The expression of VEGFRA gene in the experimental group relative to the control group was 84.07%, which indicates that after being treated with the cowhide peptide, the experimental group inhibited the expression of the VEGFA gene under the stimulation of blue light.

The vascular endothelial growth factor A (VEGFA) plays an important role in the physiological and pathological angiogenesis of the eye. When the eye is externally stimulated, the expression of VEGFA is promoted, which results in inflammation of the eye. Certain molecules have become the targets for drug development and have been approved by the U.S. Food and Drug Administration. For example, bevacizumab is a VEGFA antibody approved for intravenous injection flit the treatment of advanced cancer. It has been widely used in the field of ophthalmology for treatment of exudative age-related macular degeneration, diabetic retinopaihy, retinal vein occlusions, retinopathy of prematurity, and other chorioretinal vascular disorders. In addition, other VEGFA inhibitors such as pegaptanib and ranihizumab were also developed specifically for intraocular use, and their safety and efficacy in humans have been confirmed.

Figure 2:
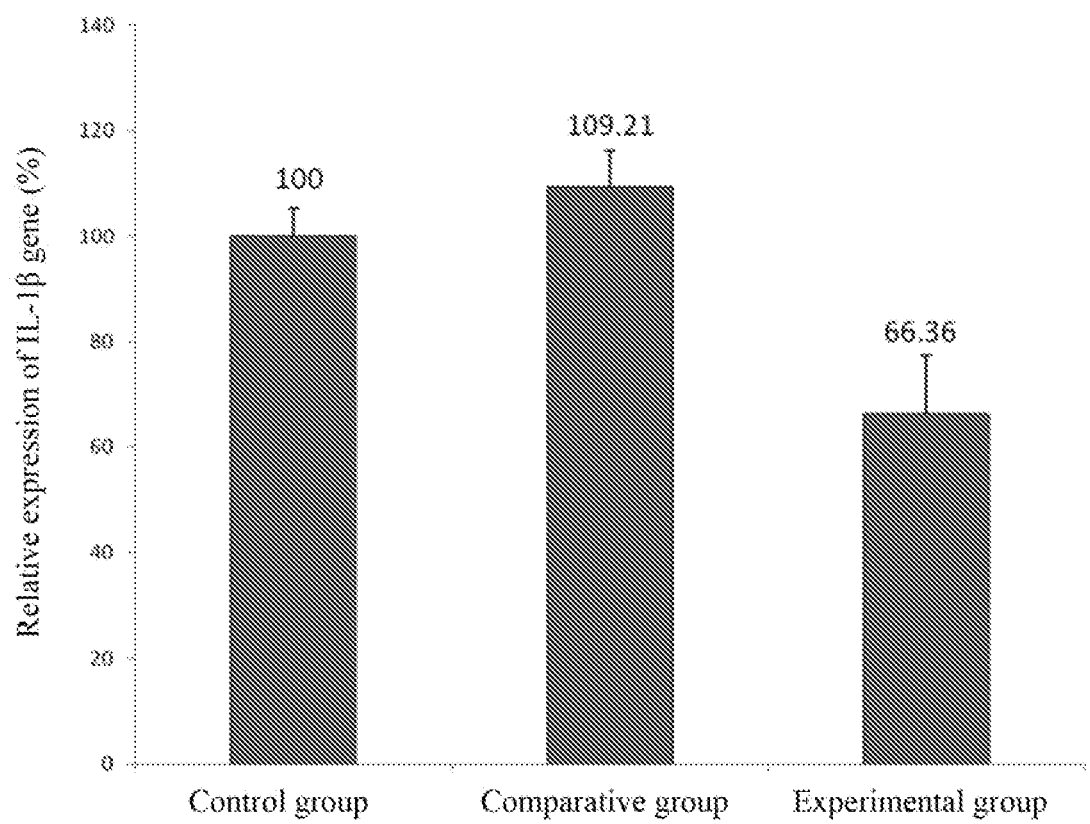
FIG. 2 is a bar chart showing a relative ratio of IL-1β gene expression in each group in Embodiment 3 of the present disclosure.

Refer to FIG. 2, when the expression of IL-1β gene in the control group is regarded as 100%, the expression of IL-1β gene in the comparative group relative to the control group is 109.21%, confirming that after irradiation with blue light, the expression of IL-1β gene in the human retinal pigment epithelial cells upregulated, and inflammation was promoted. The expression of IL-1β gene in the experimental group relative to the control group was 66.36%, which indicates that after being treated with the cowhide peptide, the experimental group inhibited the expression of IL-1β gene under the stimulation of blue light.

Figure 3:
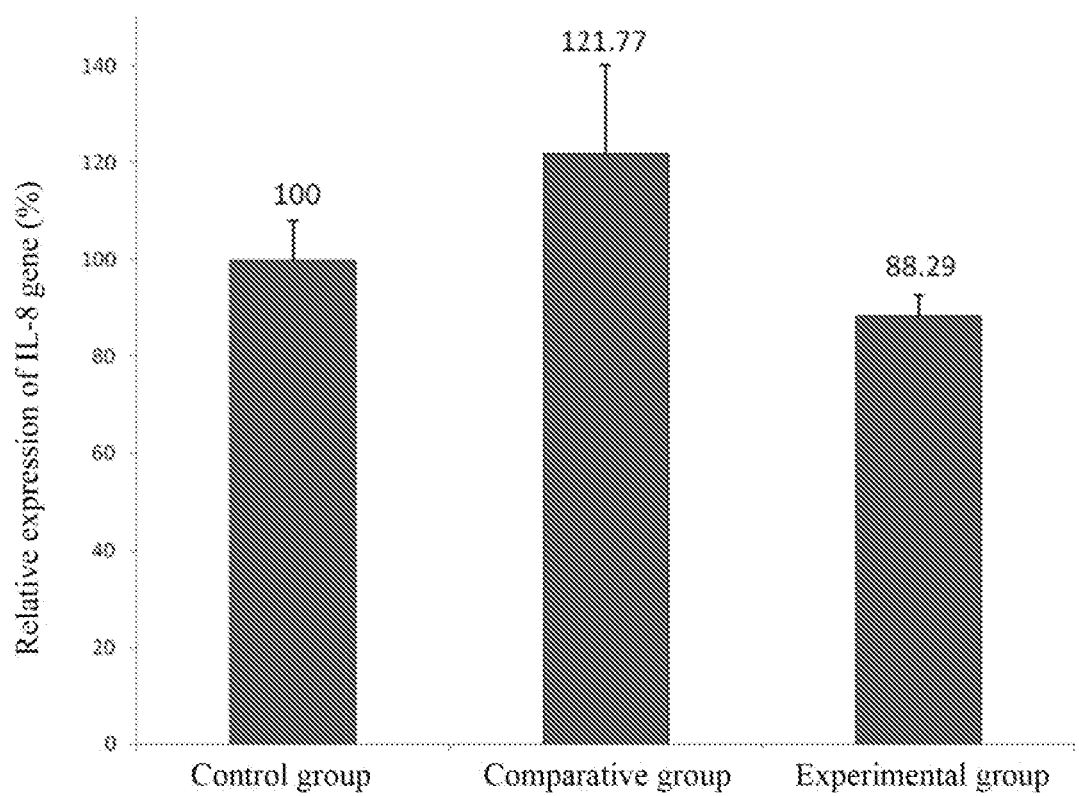
FIG. 3 is a bar chart showing a relative ratio of IL-8 gene expression in each group in Embodiment 3 of the present disclosure.

Refer to FIG. 3, when the expression of IL-8 gene in the control group is regarded as 100%, the expression of IL-8 gene in the comparative group relative to the control group is 121.77%, confirming that after irradiation with blue light, the expression of IL-8 gene in the human retinal pigment epithelial cells upregulated, and inflammation was promoted. The expression of IL-8 gene in the experimental group relative to the control group was 88.29%, which indicates that after being treated with the cowhide peptide, the experimental group inhibited the expression of IL-8 gene under the stimulation of blue light.

IL-1β is an important pro-inflammatory factor in the interleukin family protein. After innate immune cells are activated by Toll-like receptors or RIG-like receptors, precursors of IL-1β would be synthesized, and become active IL-1β after being modified by protease, therefore promoting inflammation. IL-8 is a cytokine secreted by macrophages and epithelial cells. IL-8 binds with chemokine receptors interleukin-8 receptor α (IL8RA, also known as CXCR1) and interleukin-8 receptor β (IL-8RB, also known as CXCR2) to cause chemotactic effects on neutrophils and regulate inflammation. IL-8 has a strong angiogenesis effect, and plays an important role in the pathology of inflammatory diseases, such as bronchitis and cystic fibrosis. Cytokinesi-chemokines such as IL-1β and IL-8 have been confirmed to relate to the inflammatory mechanism of eye irritation. When the human body suffers eye irritation due to environmental exposure, the expression of IL-1β and IL-8 proteins upregulates, and causes inflammation of the eye, resulting in symptoms such as swelling of the eyelid, bloodshot eyes, and allergic conjunctivitis.

The results shown in FIG. 1 to FIG. 3 demonstrate that after stimulation with blue light, the expressions of VEGFA gene, IL-1β gene and IL-8 gene of the comparative group not treated with the cowhide peptide of the present disclosure all had upregulated to promote inflammation. However, as compared with the comparative group, the expressions of VEGFA gene, IL-1β gene and IL-8 gene in the experimental group all decreased after treatment with blue light, indicating that the cowhide peptide as the bioactive compound of the present disclosure can resist blue light and reduce the expression of eye inflammation-related genes. Therefore, the results confirm that the cowhide peptide of the present disclosure is effective in eye protection and anti-inflammation, and can achieve the effects of resisting blue light, relieving eye fatigue, preventing eye inflammation, and reducing light damage to the eyes.

In summary, the peptide having the amino acid sequence of SEQ ID NO.: 1 according to any of the embodiments of the present disclosure can be used as the bioactive compound for treating inflammation. In some embodiments, the amino acid sequence may be isolated and purified from cowhide cells, cowhide collagen, or beef cells. In some embodiments, the peptide as the bioactive compound can reduce the expression of inflammation-related genes, including at least one of vascular endothelial growth factor A (VEGFA) gene, interleukin-1 beta (IL-1β) gene and interleukin-8 (IL-8) gene. The composition of the embodiment of the present disclosure has eye protective effects, such as preventing eye inflammation, resisting blue light, relieving eye fatigue and reducing light damage to the eye.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for treating eye inflammation in a human in need thereof, comprising administering to the human a therapeutically effective amount of an anti-inflammatory composition, the anti-inflammatory composition comprising a bioactive compound, the bioactive compound being a peptide having an amino acid sequence as set forth in SEQ ID NO.: 1.

2. The method according to claim 1, wherein the amino acid sequence is isolated from cowhide cells, cowhide collagen, or beef cells.

3. The method according to claim 1, wherein the amino acid sequence is synthesized by Fmoc-solid phase peptide synthesis.

4. The method according to claim 1, wherein the anti-inflammatory composition reduces expression of at least one of vascular endothelial growth factor A (VEGFA) gene, interleukin-1beta (IL-1β) gene, and interleukin-8 (IL-8) gene in the human.

5. The method according to claim 1, Wherein a concentration of the bioactive compound in the anti-inflammatory composition is at least 0.0125 mg/ml.

6. The method according to claim 1, wherein the anti-inflammatory composition is administered to an eye of the human.

7. The method according to claim 1, wherein the anti-inflammatory composition is a medicament, a food or a skincare product.

8. The method according to claim 7, wherein the food is a health food.

* * * * *